(12) United States Patent
Sakhrani et al.

(10) Patent No.: US 8,084,103 B2
(45) Date of Patent: Dec. 27, 2011

(54) METHOD FOR TREATING A HYDROPHILIC SURFACE

(76) Inventors: Vinay G. Sakhrani, Raleigh, NC (US); Charles Tomasino, Raleigh, NC (US)

( * ) Notice: Subject to any disclaimer, the term of this patent is extended or adjusted under 35 U.S.C. 154(b) by 406 days.

(21) Appl. No.: 12/354,950

(22) Filed: Jan. 16, 2009

(65) Prior Publication Data

US 2009/0126404 A1    May 21, 2009

Related U.S. Application Data

(63) Continuation-in-part of application No. 11/464,819, filed on Aug. 15, 2006, now abandoned.

(51) Int. Cl.
*H05H 1/24* (2006.01)
*C03C 17/00* (2006.01)
*C03C 17/34* (2006.01)

(52) U.S. Cl. ........... 427/535; 65/60.1; 65/60.2; 427/569

(58) Field of Classification Search .......... 65/30.1
See application file for complete search history.

(56) References Cited

U.S. PATENT DOCUMENTS

| | | | |
|---|---|---|---|
| 4,368,313 A | 1/1983 | Hayes | |
| 4,536,179 A | 8/1985 | Anderson et al. | |
| 4,688,935 A | 8/1987 | Barnes | |
| 4,767,414 A | 8/1988 | Williams et al. | |
| 4,822,632 A | 4/1989 | Williams et al. | |
| 4,842,889 A | 6/1989 | Hu et al. | |
| 4,844,986 A | 7/1989 | Karakelle et al. | |
| 4,960,609 A | 10/1990 | Homola et al. | |
| 5,041,304 A | 8/1991 | Kusano et al. | |
| 5,225,659 A | 7/1993 | Kusano et al. | |
| 5,331,487 A | 7/1994 | Gregory et al. | |
| 5,338,312 A | 8/1994 | Montgomery | |
| 5,409,738 A | 4/1995 | Matsunuma et al. | |
| 5,591,481 A | 1/1997 | Takahashi et al. | |
| 5,733,610 A * | 3/1998 | Okazaki et al. | 427/569 |
| 5,830,577 A | 11/1998 | Murayama et al. | |
| 5,895,558 A | 4/1999 | Spence | |
| 5,958,544 A * | 9/1999 | Usuki | 428/832.4 |
| 6,090,081 A | 7/2000 | Sudo et al. | |
| 6,221,434 B1 | 4/2001 | Visca et al. | |
| 6,558,889 B1 | 5/2003 | Oishi et al. | |
| 6,613,394 B2 | 9/2003 | Kuckertz et al. | |
| 2004/0231926 A1* | 11/2004 | Sakhrani et al. | 184/18 |
| 2008/0038484 A1 | 2/2008 | Alcott | |
| 2008/0044588 A1 | 2/2008 | Sakhrani | |
| 2008/0254304 A1 | 10/2008 | Sakhrani | |

FOREIGN PATENT DOCUMENTS

| | | |
|---|---|---|
| JP | 05-140573 | 6/1993 |
| JP | 11-342371 | 12/1999 |
| JP | 2000-057564 | 2/2002 |
| JP | 2002-224735 | 8/2002 |

* cited by examiner

*Primary Examiner* — Matthew Daniels
*Assistant Examiner* — Cynthia Szewczyk
(74) *Attorney, Agent, or Firm* — Law Office of David P. Hendricks

(57) ABSTRACT

One embodiment comprises a method for increasing the hydrophobic characteristics of a surface. A coupling agent is applied to the surface, and the surface is subsequently exposed to a first ionizing gas plasma at about atmospheric pressure for a predetermined period of time. The ionizing gas plasma may be formed from a mixture of a carrier gas and a reactive gas. The reactive gas may be comprised of one or more hydrocarbon compound such as an alkane, an alkene, and an alkyne. Alternatively, the reactive gas may be a fluorocarbon or organometallic compound. A lubricant may then be applied to the surface, followed by exposure to second ionizing gas plasma.

20 Claims, 6 Drawing Sheets

METHOD FOR TREATING A HYDROPHILIC SURFACE

CROSS-REFERENCE TO RELATED APPLICATIONS

The present application is a continuation-in-part of U.S. patent application Ser. No. 11/464,819 filed on Aug. 15, 2006 and is related to U.S. Pat. No. 7,431,989 issued on Oct. 7, 2008, entitled "Article with Lubricated Surface and Method," which is incorporated herein by reference it its entirety.

BACKGROUND

It is well known in the art that friction is the resistant force that prevents two objects from sliding freely when in contact with one another. There are a number of different types of frictional forces depending upon the particular motion being observed. Static friction is the force that holds back a stationary object up to the point where the object begins to move. Kinetic friction is the resistive force between two objects in motion that are in contact with one another. For any two objects in contact with one another, a value known as the coefficient of friction can be determined which is a relative measure of these frictional forces. Thus, there is a static coefficient of friction and a kinetic coefficient of friction. Stated another way, the coefficient of friction relates to the amount of force necessary to initiate movement between two surfaces in contact with one another, or to maintain this sliding movement once initiated. Because of their chemical composition, physical properties, and surface roughness, various objects have different coefficients of friction. Softer, more compliant materials such as rubber and elastomers tend to have higher coefficient of friction values (more resistance to sliding) than less compliant materials. The lower the coefficient of friction value, the lower the resistive force or the slicker the surfaces. For example, a block of ice on a polished steel surface would have a low coefficient of friction, while a brick on a wood surface would have a much higher coefficient of friction.

The difference between the static and kinetic coefficients of friction is known as "stick-slip." The stick-slip value is very important for systems that undergo back-and-forth, stop-and-go, or very slow movement. In such systems, a force is typically applied to one of the two objects that are in contact. This force must be gradually increased until the object begins to move. At the point of initial motion, referred to as "break-out," the static friction has been overcome and kinetic frictional forces become dominant. If the static coefficient of friction is much larger than the kinetic coefficient of friction, then there can be a sudden and rapid movement of the object. This rapid movement may be undesirable. Additionally, for slow moving systems, the objects may stick again after the initial movement, followed by another sudden break-out. This repetitive cycle of sticking and break-out is referred to as "stiction."

In order to minimize the friction between two surfaces, a lubricant can be applied which reduces the force required to initiate and maintain sliding movement. However, when two lubricated surfaces remain in contact for prolonged periods of time, the lubricant has a tendency to migrate out from the area of contact due to the squeezing force between the two surfaces. This effect tends to increase as the squeezing force increases. As more of the lubricant migrates from between the two surfaces, the force required to initiate movement between the surfaces can revert to that of the non-lubricated surfaces, and stiction can occur. This phenomenon can also occur in slow moving systems. Because of the slow speed, the time interval is sufficient to cause the lubricant to migrate away from the area of contact. Once the object moves past the lubricant-depleted area, the object comes into contact with a lubricant-rich area. The frictional force is less in the lubricant-rich area and sudden, rapid movement of the object can occur.

Attempts have been made to reduce the migration of lubricant from between surfaces in contact with one another. In particular, methods exist using an energy source to treat a lubricant applied to one or more of the surfaces such that the migration is reduced.

Information relevant to attempts to address the above problems using a gas plasma as the energy source for several specific embodiments can be found in the following U.S. Pat. Nos. 4,536,179; 4,767,414; 4,822,632; 4,842,889; 4,844,986; 4,876,113; 4,960,609; 5,338,312; and 5,591,481. However, each one of these references suffers from the disadvantage of treating the lubricant layer with an ionizing gas plasma generated under vacuum, rendering the methods impractical for large-scale production operations.

A need exists, therefore, for a method to produce a lubricated surface in which the migration of lubricant from the area of contact between two surfaces is reduced such that the break-out force and sliding frictional force are minimized, such method not being conducted under vacuum. A need also exists for articles produced by such a method.

SUMMARY

The inventors of the present invention are co-inventors of U.S. Pat. No. 7,431,989, entitled "Article with Lubricated Surface and Method" which is hereby incorporated by reference in its entirety. U.S. Pat. No. 7,431,989 has proved useful for lubricating medical syringes. Medical syringes are typically used in two general ways. In the first, the syringe is filled with liquid, then the liquid is dispensed almost immediately. In the second, commonly known as pre-filled syringes, the syringe is filled with liquid then stored for a length of time. While the invention of U.S. Pat. No. 7,431,989 may be used in either case, it has been discovered that a new and novel method may be used in conjunction with the invention of U.S. Pat. No. 7,431,989 to further enhance the stability of the lubricant layer on hydrophilic surfaces such as glass. In particular, the present invention is useful when the liquid is stored in the syringe for a length of time.

One embodiment of the present invention comprises a method to lubricate a surface by applying a coupling agent to the surface, exposing the surface to a first ionizing gas plasma at about atmospheric pressure, applying a lubricant to the surface, and exposing the surface to a second ionizing gas plasma at about atmospheric pressure. Either of the first and second ionizing gas plasmas may be generated from a process gas that may be comprised of one or more carrier gases and/or one or more reactive gases. The carrier gas may be comprised of one or more inert gases, and the reactive gas may be comprised of one or more hydrocarbon, fluorocarbon, or organometallic compounds. In one embodiment the coupling agent is a silane coupling agent. One embodiment comprises applying the coupling agent to the surface, followed by application of the lubricant. The surface is then exposed to an ionizing gas plasma at about atmospheric pressure.

DESCRIPTION

Figure 1:
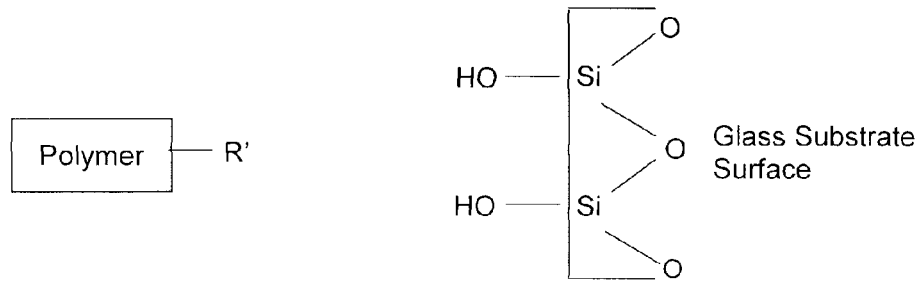
FIG. 1 is a schematic diagram of a polymer and a glass substrate according to one embodiment.

In the description that follows, a number of terms are used. In order to provide a clear and consistent understanding of the specification and appended claims, including the scope to be given such terms, the following definitions are provided:

About Atmospheric Pressure. An embodiment of the invention involves the generation of an ionizing gas plasma. While gas plasmas can be produced under various levels of vacuum, the invention uses a plasma generated at essentially atmospheric pressure. While no conditions of vacuum or above-atmospheric pressure are deliberately produced by carrying out the method of the invention, the characteristics of the gas flow may create a deviation from atmospheric pressure. For example, when using a method of the invention to treat the inside of a cylindrical object, the gas flowing into the cylinder may result in a higher pressure within the cylinder than outside the cylinder.

Break-Out. An embodiment of the invention involves surfaces in sliding contact with one another. When the surfaces are in contact but at rest, a force must be applied to one of the surfaces to initiate movement. This applied force must be increased until the frictional forces opposing movement are overcome. The point at which the applied force just surpasses the frictional force and movement is initiated is known as break-out.

Chatter. Repetitive stick-slip movement associated with the movement of surfaces in contact with one another is known as chatter. When a lubricant is present between the surfaces, chatter can occur when the lubricant is squeezed out from between the surfaces, resulting in an increase in the coefficient of friction. A larger force must then be applied to the surfaces in order to initiate movement, which can cause a sudden, exaggerated movement. Chatter occurs when this cycle is repetitive.

Coefficient of Friction. The coefficient of friction relates to the amount of force necessary to initiate movement between two surfaces in contact with one another, or to maintain this sliding movement once initiated. Numerically, the term is defined as the ratio of the resistive force of friction divided by the normal or perpendicular force pushing the objects together.

Electron Beam Radiation. Electron beam radiation is a form of ionizing radiation produced by first generating electrons by means of an electron gun assembly, accelerating the electrons, and focusing the electrons into a beam. The beam may be either pulsed or continuous.

Friction. Friction is a resistive force that prevents two objects from sliding freely against each other.

Functionalized Perfluoropolyether. A perfluoropolyether which contains one or more reactive functional groups.

Gamma Radiation. Gamma radiation is a type of electromagnetic waveform, often emitted at the same time the unstable nucleus of certain atoms emits either an alpha or beta particle when the nucleus decays. Gamma radiation, being an electromagnetic waveform, is similar to visible light and x-rays but of a higher energy level which allows it to penetrate deep into materials.

Gas Plasma. When sufficient energy is imparted to a gas, electrons can be stripped from the atoms of the gas, creating ions. Plasma contains free-moving electrons and ions, as well as a spectrum of electrons and photons.

Ionizing. Ionizing means that enough energy is present to break chemical bonds.

Lubricant-Solvent Solution (coating solution). The lubricant may be diluted with an appropriate solvent prior to applying the lubricant onto the surface. The resulting mixture of lubricant and solvent is known as a lubricant-solvent solution.

Parking. Syringes used in medical applications are often pre-filled prior to use and stored. The amount of time between filling the syringe and discharging the syringe is known as parking time. In general, parking increases the break-out force.

Perfluoropolyether. A perfluoropolyether is a compound with the general chemical structure of:

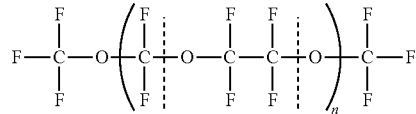

Stick-Slip. The difference between static and kinetic coefficients of friction is known as stick-slip. In systems where a lubricant is present, high mating forces can squeeze the lubricant out from between the surfaces in contact with one another. An increased force is then required to initiate sliding movement of the surfaces. This movement may occur suddenly, caused by the surfaces coming into contact with a lubricant-rich area. If the lubricant is again forced out from between the surfaces, they can begin to bind. The sliding motion can stop until the force is increased enough to once again initiate movement. This alternating sticking and slipping is called stick-slip.

Stiction. The overall phenomenon of stick-slip is known as stiction.

A method has been described in U.S. Pat. No. 7,431,989 for reducing the migration of lubricant from between surfaces in contact with one another, which comprises applying a lubricant to one or more of the surfaces, then treating the lubricant-coated surface by exposing it to an energy source. Another embodiment described in that patent comprises exposing the surface to an energy source, specifically an ionizing gas plasma at about atmospheric pressure, prior to the application of the lubricant. It is theorized that exposing the surface to the ionizing gas plasma at about atmospheric pressure prior to applying the lubricant creates active sites on the surface that facilitate the reduced migration of the lubricant. As a result of these methods, the lubricant resists migrating from between the surfaces in contact with one another, thereby reducing the break-out force and sliding frictional force.

Further experimentation has shown that, on hydrophilic surfaces such as glass, a thin layer of water may form on the surface after the surface is exposed to an energy source and prior to application of the lubricant. Indeed, a layer of water may always be present on the glass surface under ambient conditions. Subsequent application of the lubricant over the water layer may lead to increased migration of the lubricant between surfaces in contact with one another. It is theorized that the water layer lessens the retention of the lubricant layer on the surface as achieved by the methods of U.S. Pat. No. 7,431,989. Water, which may be present in the air surrounding the surface, condenses on the surface almost immediately after exposure to the energy source unless the surface is maintained at a temperature of at least about 130° C. Maintaining such temperatures are impractical in a large-scale production environment.

Experimentation has also shown that when a medical syringe made of glass is filled with a liquid and the plunger is parked for a length of time, the liquid has a tendency to migrate under the lubricant layer and lessen the bond strength of the lubricant to the glass surface. This phenomenon is the result of the hydrophilic nature of the glass surface. The liquid in the syringe has a tendency to wet the glass surface because of the surface's hydrophilic nature. The present invention serves to modify the surface characteristics of the glass to increase its hydrophobicity. As such, the affinity between the glass surface and the liquid stored in the syringe is reduced and the liquid no longer tends to wet the glass surface. This minimizes the migration of the liquid under the lubricant layer and allows the invention of U.S. Pat. No. 7,431,989 to work as well with filled and parked syringes as those that are used immediately after filling.

In one embodiment of the present invention, the energy source is an ionizing gas plasma comprised of one or more carrier gases and one or more reactive gases. The carrier gas may be a noble gas including, for example, helium, neon, argon, krypton, and xenon. Alternatively, the carrier gas may be an oxidative gas including, for example, air, oxygen, carbon dioxide, carbon monoxide, and water vapor. In yet another alternative, the carrier gas may be a non-oxidative gas including, for example, nitrogen and hydrogen. Mixtures of any of these carrier gases may also be used.

The reactive gas may be any hydrocarbon gas, such as an alkane represented by the chemical formula $C_nH_{2n+2}$, an alkene represented by the chemical formula $C_nH_{2n}$, and an alkyne represented by the chemical formula $C_nH_{2n-2}$. Examples of alkanes are methane, ethane, propane, butane, and the like. Examples of alkenes are ethylene, propylene, isobutylene, and the like. Examples of alkynes are ethyne (acetylene), propyne, 1-butyne, and the like. Additionally, the reactive gas may be fluorocarbon compound, wherein one or more of the hydrogen atoms in the above listed hydrocarbon compounds are replaced with a fluorine atom. Examples of these fluorochemical compounds are tetrafluoromethane, tetrafluoroethylene, and hexafluoropropylene. Additionally, the reactive gas may be an organometallic compound. Examples of organometallic compounds are tetramethylsilane and hexamethyldisiloxane. Mixtures of any of these reactive gases may also be used.

The method according to one embodiment of the present invention comprises applying a coupling agent to the hydrophillic surface prior to exposing the surface to the ionizing gas plasma. In one embodiment, the coupling agent is a silane coupling agent. Silane coupling agents have the ability to form a bond between organic materials and inorganic materials such as materials with siliceous properties. A common inorganic material suitable for one embodiment of the present invention is glass.

The general chemical structure of a silane coupling agent is $R-(CH_2)_n-Si-X_3$. This structure illustrates the two classes of functionality typical to coupling agents. The R group may be a nonhydrolyzable organofunctional group linked to the silicon atom via a silicon-carbon bond. The functionality of the R group is selected to impart desired characteristics, such as increasing the hydrophobic property of the inorganic surface or provide the ability to bond with an organic polymer. The X group may be a hydrolyzable group capable of forming silanol groups (Si—OH). Silanol groups may bond with hydroxyl groups on polymeric surfaces such as siliceous materials. The hydrolyzable groups may be halogens, alkoxy (—O—R), or acyloxy (—O—COR). Each of these groups is capable of reacting with water to form silanols that in turn may condense to form siloxane linkages or react with hydroxyl groups on polymeric surfaces.

Figure 2:
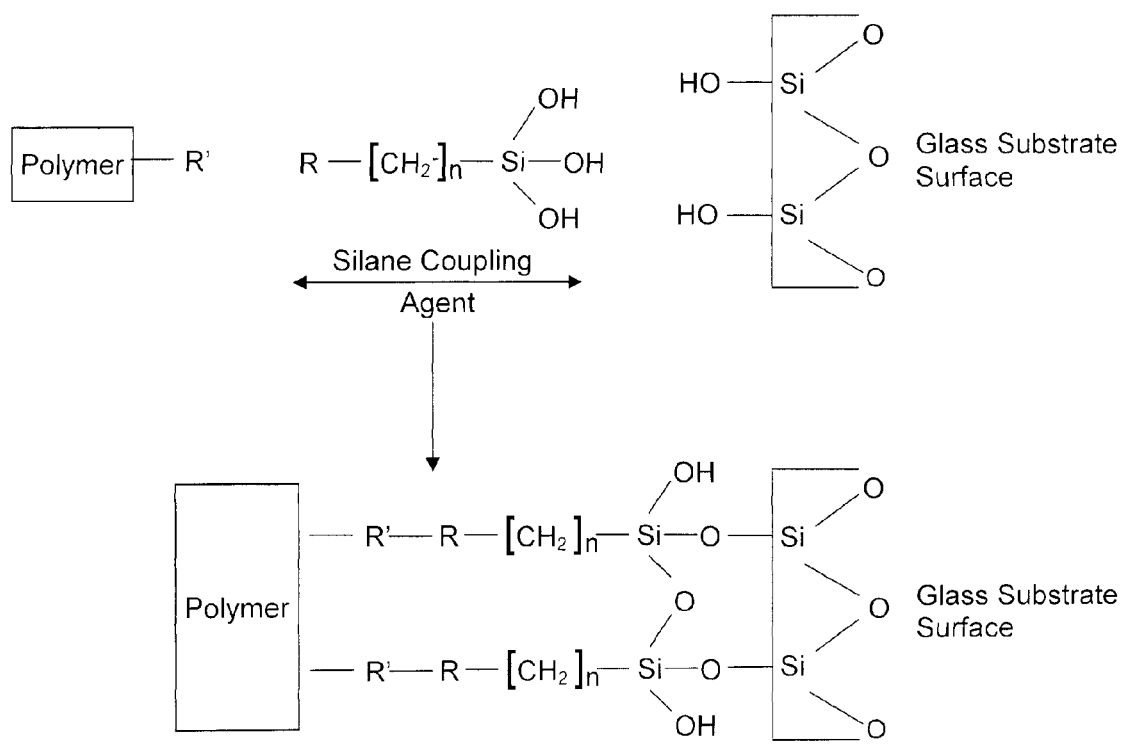
FIG. 2 is a schematic diagram of the function of a silane coupling agent according to one embodiment.

FIGS. 1 and 2 schematically illustrate the function of a silane coupling agent in conjunction with glass as the inorganic material. FIG. 1 illustrates a polymer compound with an organofunctional group R' that is desired to be bonded to the glass substrate. The R' group of the polymer has a very low affinity for the hydroxyl groups (—OH) of the glass substrate. Thus, little or no bonding may occur between the polymer and the glass substrate. While the polymer may be applied to the glass substrate, the lack of bonding between the two allows the polymer to be easily removed from the glass substrate. As an example, a silicone lubricant may be applied to the barrel of a glass syringe, but movement of the stopper within the barrel will wipe the lubricant from the glass surface.

In FIG. 2, the silane coupling agent includes an organofunctional group R that may bond with the organofunctional group R' of the polymer. The coupling agent also includes hydrolyzable groups (—OH groups as illustrated in FIG. 2) capable of bonding with the substrate. In this embodiment, the hydrolyzable groups are hydrolyzed to form silanol-containing species. Condensation to oligomers then occurs, and the oligomers hydrogen bond with the —OH groups of the substrate. A drying or curing step may then occur, forming a covalent linkage between the coupling agent and the substrate. Because the polymer adheres to the organofunctional group R of the coupling agent, the polymer is effectively bonded to the glass substrate. Again using the example of the glass syringe barrel, a polymer (e.g., a perfluoropolyether lubricant) may better adhere to the syringe barrel using a coupling agent such that most if not all of the polymer remains in place on the syringe barrel when the stopper is moved within the syringe barrel. As used herein, the term "adhere" simply refers to the polymer remaining in place on the glass surface when subjected to mechanical forces, such as the forces imparted by moving the stopper within the syringe barrel. The use of the term should not be construed to imply any particular adhesive mechanism, whether mechanical or chemical, and no limitations are to be implied.

Typically, silane coupling agents have one organofunctional group (R) and three hydrolyzable groups (X) as illustrated in the above general chemical structure. The reaction of the coupling agent is typically a four-step process that begins by hydrolyzing the three hydrolyzable groups to form silanol-containing species such as R—Si—(OH)$_3$. Condensation of the silanol-containing species to oligomers then follows. The oligomers then form hydrogen bonds with hydroxyl groups (—OH) of the substrate. In the final step, drying or curing occurs during which water is lost and a covalent linkage is formed between the coupling agent and the substrate.

There are at least two general classes of silane coupling agents that may be beneficially used with the present invention. The first class is know as hydrophobic silanes. The hydrophobic silanes may be further classified according to the number of carbon atoms in the organofunctional group (R) and the structure of the hydrolyzable group (X). The organofunctional group in case of a hydrophobic silane may be a methyl group, linear alkyl group of the general formula $CH_3(CH_2)_n$ where n=1 to about 33, branched or cyclic alkyl group, phenyl group, phenyl alkyl group, or napthyl group. The hydrolyzable group may be a chloro group, methoxy group, ethoxy group, propoxy group, butoxy group, acetoxy group, amine group, or silizane group.

The second general class of silane coupling agents is unsaturated silanes. These silanes may be classified similarly to the classification of the hydrophobic silanes. The organofunctional group in the case of an unsaturated silane may be an allyl group, acryloxy group, methacryloxy group, or vinyl group. In addition, vinyl silanes may include an acetoxy hydrolyzable group. The above list of hydrophobic and unsaturated silanes are provided as examples and are not intended to be limiting in any way. Other silane coupling agents may be used in the present application.

Non-limiting examples of specific silane coupling agents that may be used in the present invention include methyltrichlorosilane, methyltriacetoxysilane, methyltrimethoxysilane, methyltriethoxysilane, ethyltrichlorosilane, ethyltriacetoxysilane, ethyltrimethoxysilane, ethyltriethoxysilane, propyltrichlorosilane, propyltrimethoxysilane, propyltriethoxysilane, octadecyltrichlorosilane, octadecyltrimethoxysilane, octadecyltriethoxysilane, isobutyltrichlorosilane, isobutyltrimethoxysilane, t-butyltrichlorosilane, isopentyltrichlorosilane, cyclohexyltrichlorosilane, cyclohexyltrimethoxysilane, phenyltrichlorosilane, phenyltrimethoxysilane, phenyltriacetoxysilane, phenyltriethoxysilane, p-tolyltrichlorosilane, p-tolyltrimethoxysilane, 1-napthyltrimethoxysilane, (1-napthylmethyl)trichlorosilane, diethyldichlorosilane, diethyldiethoxysilane, dibutyldichlorosilane, dibutyldimethoxysilane, acetoxyethyltrichlorosilane, acetoxyethyltrimethoxysilane, ethoxyethyltriethoxysilane, acryloxymethyltrimethoxysilane, (3-acryloxypropyl)trichlorosilane, (3-acryloxypropyl)trimethoxysilane, allydimethoxysilane, allyldichlorosilane, allylmethyltrichlorosilane, allyltrichlorosilane, allyltrimethoxysilane, allyltriethoxysilane, methylacryloxymethyltriethoxysilane, methacryloxymethyltrimethoxysilane, methylacryloxypropyltriethoxysilane, methacryloxypropyltrimethoxysilane, vinyltrichlorosilane, vinyltriacetoxysilane, vinyltrimethoxysilane, vinyltriethoxysilane, divinyldichlorosilane, 1,3-divinyltetraethoxydisolanane, 1-8-bis(trimethoxysilyl)octane, 1-8-bis(triethoxysilyl)octane, 1-6-bis(trimethoxysilyl)hexane, 1-6-bis(triethyoxysilyl)hexane, 1-2-bis(trimethoxysilyl)decane, bis(trimethoxysilyl)ethane, bis(3-trimethoxysilylpropyl)amine, N,N'-bis[(3-trimethoxysilylpropyl)]ethylenediamine, methacryloxypropyl triethoxysilane, acryloxypropyl triethoxysilane, methacryloxymethyl triethoxysilane, acryloxymethyl triethoxysilane, vinyl triethoxysilane, ethyl triacetoxysilane, and n-octadecyl trimethoxysilane.

In one embodiment, the silane coupling agent is a polymeric perfluoroether disilane such as FluoroSyl™ FSD-2500 and FSD-4500 available from Cytonix Corporation, Beltsville, Md. and Fluorolink S10 from Solvey Solexis, Inc. In one embodiment, the silane coupling agent is a polymeric perfluoroether polysilane such as FluorSyl™ FSQ-3000 available from Cytonix Corporation, Beltsville, Md.

The ionizing gas plasma may be generated using at least one carrier gas and/or at least one reactive gas. The reactive gas concentration may range from about 0.001 percent to about 10 percent. The time the surface is exposed to the ionizing gas plasma may range from about 0.1 second to about 5 minutes. The ionizing gas plasma deposits a layer of material directly onto the coupling agent, creating a barrier between the surface and the water in the air, as opposed to creating active bonding sites as in the method of U.S. Pat. No. 7,431,989. Thus, the surface is now hydrophobic and nearly no water layer forms on the surface. The cross-linked lubricant layer formed by the method of U.S. Pat. No. 7,431,989 may be applied to the barrier layer without interference from a water layer. Additionally, liquid is prevented from migrating under the cross-linked lubricant layer because the liquid no longer has a tendency to wet the glass surface due to the surface's now hydrophobic nature.

The exact parameters under which the ionizing gas plasma are generated, such as power level and gas flow rates, are not critical to the methods of the present invention. These parameters are selected based on factors including, for example, the gas in which the plasma is to be generated, the electrode geometry, frequency of the power source, and the dimensions of the surface to be treated.

The lubricant may be applied to the surface of the object by any of the numerous methods know in the art. By way of example, suitable application methods include spraying, atomizing, spin casting, painting, dipping, wiping, tumbling, and ultrasonics. The method used to apply the lubricant is not essential to the performance of the invention.

The lubricant may be a fluorochemical compound or a polysiloxane-based compound. In one embodiment of the present invention, the fluorochemical compound is a perfluoropolyether (PFPE). Representative examples of commercially available PFPE include, for example, Fomblin M®, Fomblin Y®, and Fomblin Z® families of lubricants from Solvay Solexis; Krytox® from E. I. du Pont de Nemours and Company; and Demnum™ from Daikin Industries, Limited. Table 1 presents the chemical structures of these compounds, and Table 2 presents the molecular weights and viscosities. In another embodiment of the invention of the co-pending application, the lubricant is a functionalized PFPE. Representative examples of commercially available functionalized PFPE include, for example, Fomblin ZDOL®, Fomblin ZDOL TXS®, Fomblin ZDIAC®, Fluorolink A10®, Fluorolink C®, Fluorolink D®, Fluorolink E®, Fluorolink EL10®, Fluorolink F10®, Fluorolink L®, Fluorolink L10®, Fluorolink S10®, Fluorolink T®, and Fluorolink T10®, from Solvay Solexis as shown in Table 3. In yet another embodiment of the invention of U.S. Pat. No. 7,431,989, the functionalized PFPE may be an emulsion. Representative example of commercially available functionalized PFPE emulsions are, for example, Fomblin FE-20C® and Fomblin FE-20AG® from Solvay Solexis. In another embodiment of the invention of U.S. Pat. No. 7,431,989, the polysiloxane-based compound is a silicone oil with a dimethylpolysiloxane chemical formulation of the following general chemical structure:

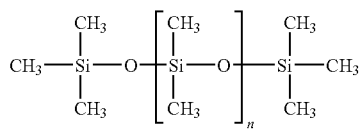

where n = 10-50,000

The number (n) of repeating siloxane units in the polymer chain will determine the molecular weight and viscosity of the silicone oil. As the number of siloxane units increases, the polymer becomes longer and both the molecular weight and viscosity increases. Generally, the usable viscosity range of silicone oils is about 5 to about 100,000 centistokes.

While the lubricant can be applied in a non-diluted form, it is often advantageous to dilute the lubricant prior to application to avoid retention of excess lubricant on the surface. For example, the lubricant can be applied to a syringe barrel by filling the barrel with the lubricant, then draining the excess lubricant from the barrel. Depending on the viscosity of the lubricant, an excessive amount of lubricant may remain in the barrel, or the time to drain the barrel may be excessive. By first diluting the lubricant, the viscosity can be controlled such that excess lubricant does not remain on the surface. Alternatively, the lubricant can be applied as a water dispersion or as an emulsion. Any suitable solvent can be used as the diluent that is compatible with the lubricant or combination of lubricants used. By way of example, a perfluorinated solvent can be used with a perfluoropolyether lubricant. The resulting mixture of one or more lubricants and one or more solvents is known as a lubricant-solvent solution. The dilution ratio, or weight percent of lubricant in the lubricant-solvent solution, will vary and depends on a number of factors including the geometry of the surface being coated, viscosity of the non-diluted lubricant, and time between coating the surface and exposing the coated surface to the energy source. The weight percent of lubricant in the solvent, when a solvent is used, may be greater than or equal to about 0.1 percent, such as, for example, 1, 10, 20, 30, 40 and 50. The weight percent of the lubricant in the solvent may also be less than or equal to about 95 percent, such as, for example, 90, 80, 70, and 60. The diluent solvent is evaporated prior to exposure to the energy source.

For commercialization purposes when a lubricant-solvent solution is used, it may be advantageous to heat the surface after applying the lubricant-solvent solution but before exposing the coated surface to the energy source. The purpose of this step is to facilitate the evaporation of the solvent. When articles are mass-produced according to the methods of the present invention, it may be necessary to minimize the time between application of the lubricant-solvent mixture and exposing the coated surface to the energy source. Therefore, the heating step will cause the solvent to evaporate quicker than at ambient conditions. While the solvent can be evaporated at ambient conditions, elevated temperatures up to about 150° C. can be used. Depending on the surface material, the heating step generally can be carried out at any convenient temperature between ambient and about 150° C., generally in the range of about 80° C. to about 130° C. The amount of time that the coated surface is heated depends on a number of factors including, by way of example, the viscosity and vapor pressure of the solvent, the thickness of the lubricant-solvent solution layer applied to the surface, and the geometric configuration of the surface. The amount of time the coated surface is heated may be greater than or equal to about 0.5 minute, such as, for example, 1, 5, 10, and 20 minutes. The amount of time the coated surface is heated may also be less than about 60 minutes, such as, for example, about 50, 40, and 30 minutes.

In addition to being diluted prior to application, the lubricant may also include additives. The additives include, for example, free radical initiators such as peroxides and azo nitriles; viscosity modifiers such as fluoroelastomers, silica, and Teflon® particles; surfactants or wetting agents; anticorrosion agents; antioxidants; antiwear agents; buffering agents; and dyes.

In one embodiment of the present invention, the lubricant-coated surface is exposed to ionizing radiation. The ionizing radiation source may be gamma radiation or electron-beam radiation. Typically, commercial gamma irradiation processing systems use cobalt-60 as the gamma radiation source, although cesium-137 or other gamma radiation source may also be used. Commercial electron-beam radiation systems generate electrons from an electricity source using an electron gun assembly, accelerate the electrons, then focus the electrons into a beam. This beam of electrons is then directed at the material to be treated. The lubricant-coated surface may be exposed to an ionizing radiation dosage ranging from about 0.1 megarad to about 20 megarads, in addition ranging from about 0.5 megarad to about 15 megarads, and further in addition ranging from about 1 megarad to about 10 megarads.

As used herein, the terms "having", "containing", "including", "comprising", and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

TABLE 1

CHEMICAL STRUCTURE OF EXAMPLE PERFLUOROPOLYETHER (PFPE) COMPOUNDS

| PFPE Compound | Chemical Structure |
| --- | --- |
| Fomblin M ® and Fomblin Z ® (Solvay Solexis) | $CF_3[(-O-CF_2-CF_2)p-(O-CF_2)q]-O-CF_3$ (p + q = 40 to 180; p/q = 0.5 to 2) |

TABLE 1-continued

CHEMICAL STRUCTURE OF EXAMPLE PERFLUOROPOLYETHER (PFPE) COMPOUNDS

| PFPE Compound | Chemical Structure |
|---|---|
| Fomblin Y ® (Solvay Solexis) | $CF_3[(-O-CF(CF_3)-CF_2)m-(O-CF_2)n]-O-CF_3$ <br> (m + n = 8 to 45; m/n = 20 to 1,000) |
| Krytox ® (E. I. du Pont de Nemours and Company) | $F-(CF(CF_3)-CF_2-O)n-CF_2-CF_3$ <br> (n = 10 to 60) |
| Demnum ™ (Daikin Industries, Limited) | $F-(CF_2-CF_2-CF_2-O)n-CF_2-CF_3$ <br> (n = 5 to 200) |

TABLE 2

MOLECULAR WEIGHT AND VISCOSITY OF EXAMPLE PERFLUOROPOLYETHER (PFPE) COMPOUNDS

| PFPE Compound | Molecular Weight (atomic mass units) | Viscosity (centistokes, 20° C.) |
|---|---|---|
| Fomblin M ® and Fomblin Z ® (Solvay Solexis) | 2,000-20,000 | 10-2,000 |
| Fomblin Y ® (Solvay Solexis) | 1,000-10,000 | 10-2,500 |
| Krytox ® (E. I. du Pont de Nemours and Company) | 500-12,000 | 7-2,000 |
| Demnum ™ (Daikin Industries, Limited) | 1,000-20,000 | 10-2,000 |

TABLE 3

FUNCTIONAL GROUPS, MOLECULAR WEIGHT, AND VISCOSITY OF FUNCTIONALIZED PERFLUOROPOLYETHER (PFPE) COMPOUNDS

| Functionalized PFPE Compound | Functional Group | Number of Functional Groups per Molecule | Molecular Weight (atomic mass units) | Viscosity (centistokes, 20° C.) |
|---|---|---|---|---|
| Fomblin ZDOL ® Fluorolink D ® (Solvay Solexis) | Alcohol $-CH_2(OH)$ | 1-2 | 1,000-4,000 | 50-150 |
| Fomblin ZDOL TXS ® Fluorolink E ® Fluorolink E10 ® (Solvay Solexis) | Alcohol $-CH_2(OCH_2CH_2)nOH$ | 1-2 | 1,000-2,500 | 80-150 |
| Fluorolink T ® Fluorolink T10 ® (Solvay Solexis) | Alcohol $-CH_2OCH_2CH(OH)CH_2OH$ | 2-4 | 1,000-3,000 | 2,000-3,000 |
| Fomblin ZDIAC ® Fluorolink C ® (Solvay Solexis) | Alkly Amide $-CONHC_{18}H_{37}$ | 1-2 | 1,800 | Wax |
| Fluorolink L ® Fluorolink L10 ® (Solvay Solexis) | Ester $-COOR$ | 1-2 | 1,000-2,000 | 10-25 |
| Fluorolink S10 ® (Solvay Solexis) | Silane | 1-2 | 1,750-1,950 | 170 |
| Fluorolink F10 ® (Solvay Solexis) | Phosphate | 1-2 | 2,400-3,100 | 18,000 |

EXAMPLE 1

Figure 3:
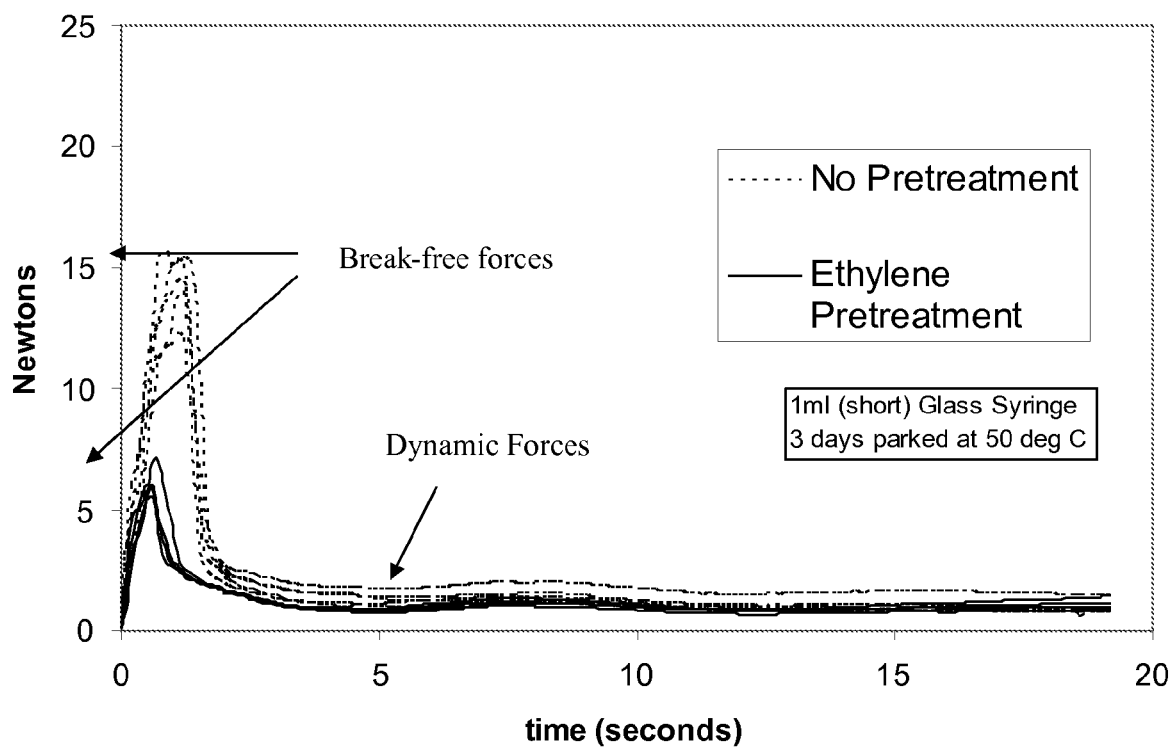
FIG. 3 is a plot of experimental measurements of the force applied to a syringe plunger as a function of infusion time, where the barrel of the syringe was coated with a specific lubricant and exposed to an ionizing gas plasma at about atmospheric plasma. In this plot, the syringe barrels were empty.
Figure 4:
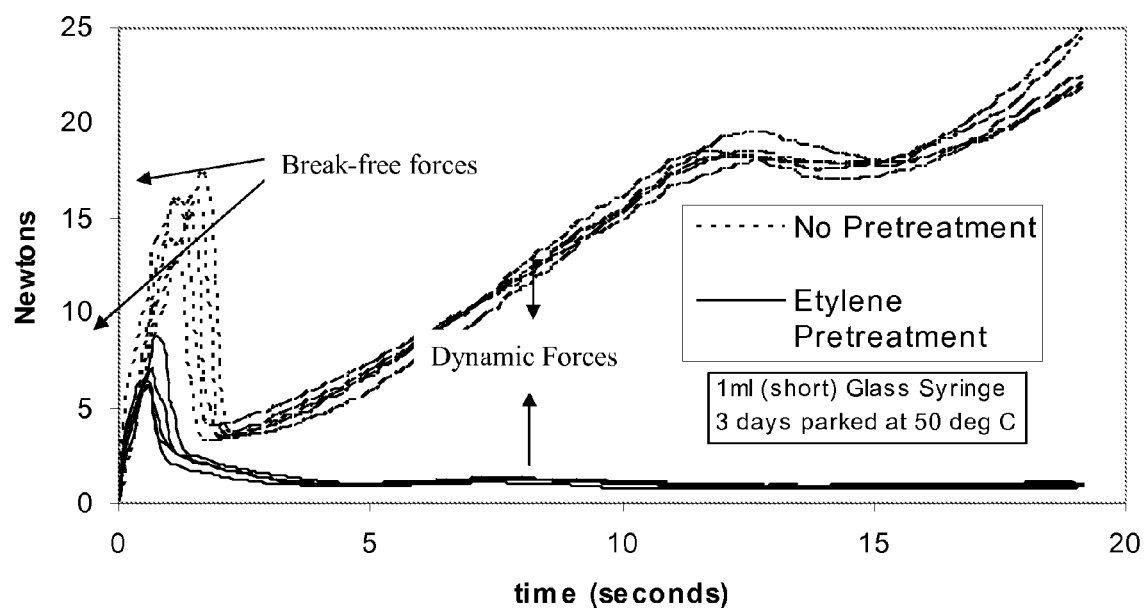
FIG. 4 is a plot of experimental measurements of the force applied to a syringe plunger as a function of infusion time, where the barrel of the syringe was coated with a specific lubricant and exposed to an ionizing gas plasma at about atmospheric plasma. In this plot, the syringe barrels were filled with DI water.

Glass Syringes—No Plasma Pretreatment (FIGS. 3 and 4)

Glass syringe barrels (size 1 ml) were sprayed with 0.3 micro liters of perfluoropolyether lubricant on the inside surfaces of the syringe barrel. These syringe barrels were then plasma treated at about atmospheric pressure using helium carrier gas but without any reactive gas for 0.5 seconds. The syringes were assembled using clean halobutyl rubber stoppers.

The treated syringes were divided into two groups. The first group was assembled empty with no fluid in them. The second group was filled with DI water. The syringe stoppers from each set were parked in one position in the barrel, and they were then stored in an oven at 50° C. for 72 hours. The syringes were removed from the oven and allowed to condition at ambient conditions for 5 hours. After conditioning, the syringe forces were measured using a Harvard Apparatus syringe pump mounted with a Dillon AFG-100N digital force gauge.

EXAMPLE 2

Figure 5:
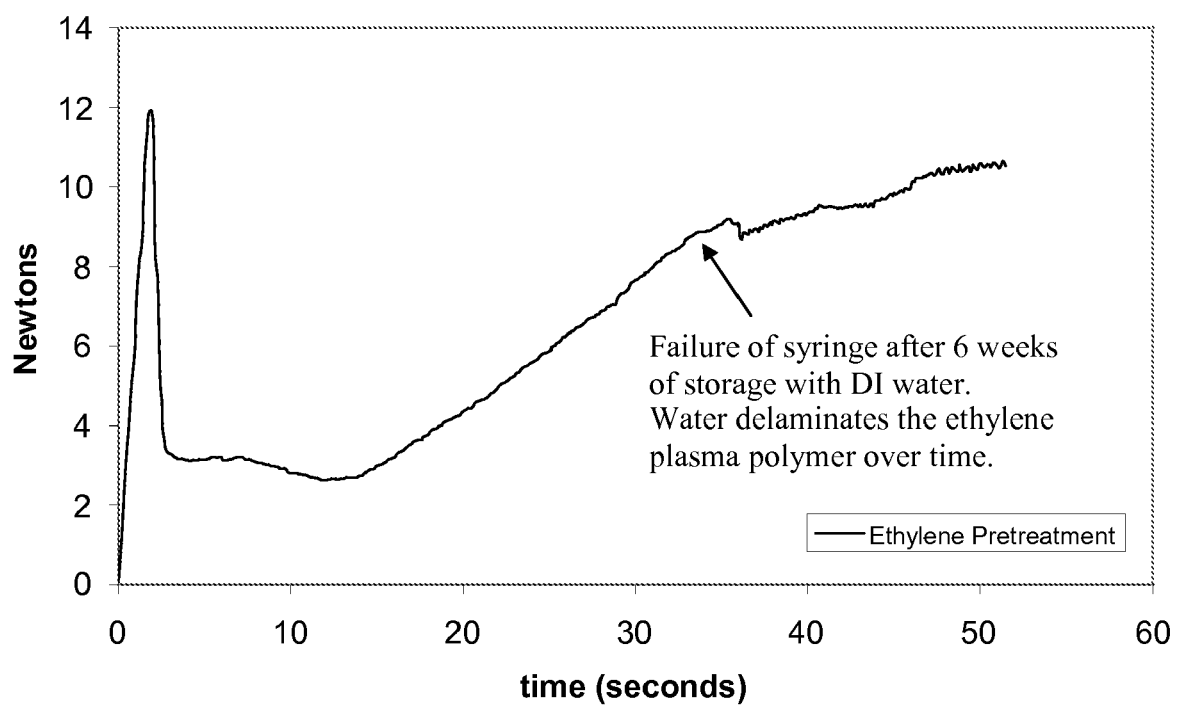
FIG. 5 is a plot of experimental measurements of the force applied to a syringe plunger as a function of infusion time, where the barrel of the syringe was exposed to an ionizing gas plasma at about atmospheric pressure, coated with a specific lubricant, and exposed to an ionizing gas plasma at about atmospheric plasma. In this plot, the syringe barrels were filled with DI water.

Glass Syringes—With Ethylene Plasma Pretreatment (FIGS. 3, 4, and 5)

Glass syringe barrels (size 1 ml) were first plasma treated at about atmospheric pressure using the following pretreatment conditions:

Reactive gas—ethylene (flow rate—4 cc/min)
Carrier gas—helium (flow rate—2 liters/min)
Plasma treatment—5 seconds To check the effectiveness of the plasma pretreatment, the inner surface of the syringes were tested for wetting with a drop of DI water. Before the pretreatment, the water contact angle was approximately 5 degrees indicating complete wetting of the surface. Following the ethylene plasma pretreatment, the contact angle was greater than 50 degrees indicating a hydrophobic surface.

Following the ethylene plasma pretreatment, the glass syringe barrels were sprayed with 0.3 micro liters of perfluoropolyether lubricant on the inside surfaces of the syringe barrel. The sprayed syringe barrels were plasma treated at atmospheric pressure using helium gas for 0.5 seconds. The syringes were assembled using clean halobutyl rubber stoppers.

The assembled pretreated syringes were divided into three groups. The first group were left empty (FIG. 3). The second group was filled with DI water and stored at 50° C. for 72 hours (FIG. 4). The third group was filled with DI water and stored at 50° C. for 6 weeks (FIG. 5). The syringes were removed from the oven and allowed to condition at ambient conditions for 5 hours. After conditioning, the syringe forces were measured using a Harvard Apparatus syringe pump mounted with a Dillon AFG-100N digital force gauge.

EXAMPLE 3

Figure 6:
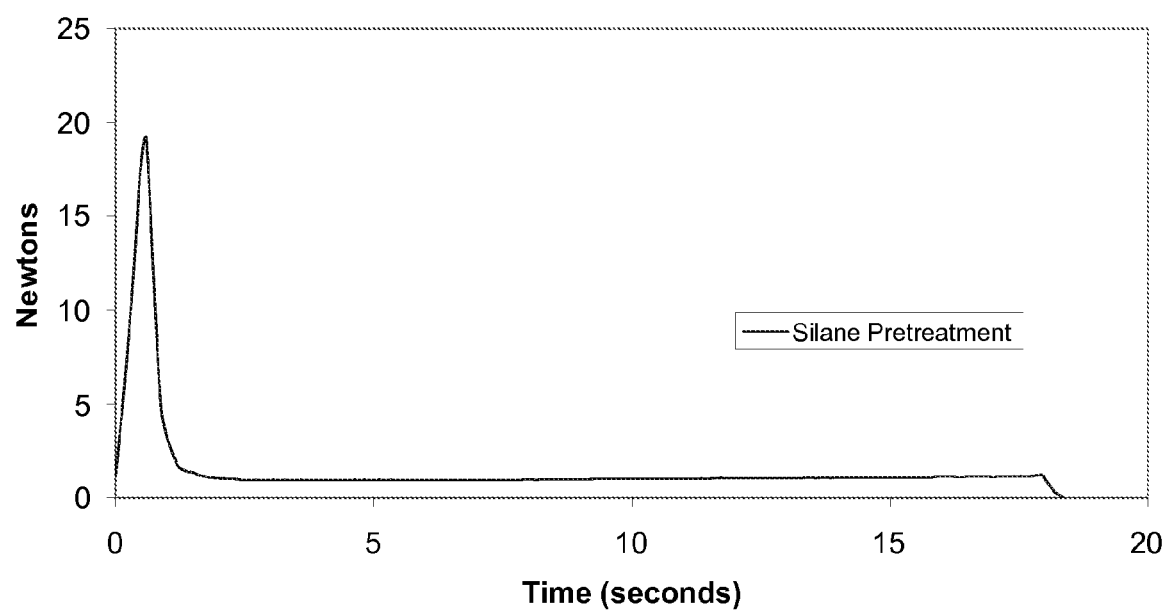
FIG. 6 is a plot of experimental measurements of the force applied to a syringe plunger as a function of infusion time, where the barrel of the syringe was coated with a coupling agent and a specific lubricant, then exposed to an ionizing gas plasma at about atmospheric plasma. In this plot, the syringe barrels were filled with DI water.

Glass Syringes—Treatment with Silane Coupling Agent, No Pretreatment (FIG. 6)

Glass syringe barrels (size 1 ml) were sprayed with 0.25% solution of n-octadecyl trimethoxy silane in isopropanol and heated at 100° C. for 5 minutes. Following the heating step, the resulting surface was found to be hydrophobic with a DI water contact angle of greater than 50°. The syringe barrels were then sprayed with 0.3 micro liters of perfluoropolyether lubricant on the inside surfaces of the syringe barrel. The sprayed syringe barrels were plasma treated at atmospheric pressure using helium gas for 0.5 seconds. The syringe barrels were assembled using clean halobutyl rubber stoppers.

The assembled syringes were then filled with DI water and stored at 50° C. for 6 weeks with the stopper parked at about the midpoint of the syringe barrel. The syringes were removed from the oven and allowed to condition at ambient conditions for 5 hours. After conditioning, the syringe forces were measured using a Harvard Apparatus syringe pump mounted with a Dillon AFG-100N digital force gauge (FIG. 6).

EXAMPLE 4

Figure 7:
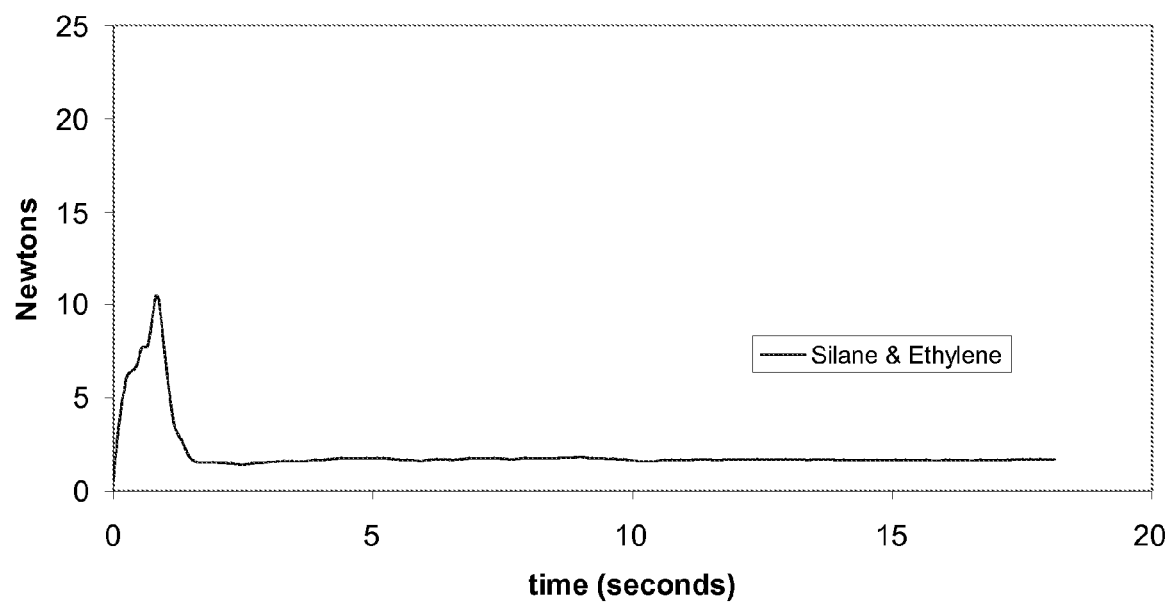
FIG. 7 is a plot of experimental measurements of the force applied to a syringe plunger as a function of infusion time, where the barrel of the syringe was coated with a coupling agent, exposed to an ionizing gas plasma at about atmospheric pressure, coated with a specific lubricant, then exposed to an ionizing gas plasma at about atmospheric plasma. In this plot, the syringe barrels were filled with DI water.

Glass Syringes—With Silane Coupling Agent and Ethylene Plasma Pretreatment (FIG. 7)

Glass syringe barrels (size 1 ml) were sprayed with 0.5% solution of methacryloxypropyl trimethoxy silane in isopropanol and heated at 100° C. for 5 minutes. Following the heating step, the resulting surface was found to be hydrophobic with a DI water contact angle of greater than 50°.

After the application of the silane coupling agent, the glass syringe barrels were plasma treated at about atmospheric pressure using the following pretreatment conditions:

Reactive gas—ethylene (flow rate—4 cc/min)
Carrier gas—helium (flow rate—2 liters/min)
Plasma treatment—5 seconds Following the ethylene plasma treatment, the syringe barrels were sprayed with 0.3 micro liters of perfluoropolyether lubricant on the inside surfaces of the syringe barrel. The sprayed syringe barrels were plasma treated at atmospheric pressure using helium gas for 0.5 seconds. The syringes were assembled using clean halobutyl rubber stoppers.

The assembled syringes were then filled DI water and stored at 50° C. for 6 weeks with the stopper parked at about the midpoint of the syringe barrel. The syringes were removed from the oven and allowed to condition at ambient conditions for 5 hours. After conditioning, the syringe forces were measured using a Harvard Apparatus syringe pump mounted with a Dillon AFG-100N digital force gauge (FIG. 7).

Discussion of Results

FIG. 3 demonstrates the syringe forces for empty syringes. One set contained syringes without any plasma pretreatment (Example 1) and the second set demonstrated forces for syringes processed with the ethylene plasma pretreatment (Example 2). The syringes were assembled "empty" without any fluid in the syringe barrels.

Results:
1. Break-free force—Ethylene pretreated syringes measures 60 percent lower force than the non-pretreated
2. Dynamic force—Both sets of syringes demonstrated comparable dynamic syringe forces.

FIG. 4 demonstrates the syringe forces for DI water filled syringes. One set contains syringes without any plasma pretreatment (Example 1), and the second set demonstrates forces for syringes processed with the ethylene plasma pretreatment (Example 2).

Results:
1. Break-free force—Ethylene pretreated syringes measured 60 percent lower force than the non-pretreated syringes.
2. Dynamic force—Without pretreatment the dynamic forces increased rapidly to unacceptably high levels. Ethylene pretreated samples demonstrate low and consistent dynamic force which are comparable to empty syringes as depicted in FIG. 3.

FIG. 5 demonstrates the syringe forces for DI water filled syringes that have been ethylene plasma pretreated and stored for an extended period (Example 2).

Results:
1. Break-free force—The break-free force of the syringes stored for 6 weeks approached that of the non-pretreated syringes.
2. Dynamic force—The dynamic force of the syringes stored for 6 weeks were not consistent and quickly increased, also indicating delamination of the ethylene plasma polymer from the glass surface. Particles of the ethylene plasma polymer were also visible in the syringe solution confirming this mode of failure.

FIG. 6 demonstrates the syringe forces for DI water filled syringes that have been treated with a silane coupling agent (0.25% solution of n-octadecyl trimethoxy silane in isopropanol) but not ethylene plasma pretreated, then stored for an extended period (Example 3).

Results:
1. Break-free force—The break-free force of the syringes stored for 6 weeks approached that of the non-pretreated syringes.
2. Dynamic force—After reaching the break-free force, the dynamic force of the syringes stored for 6 weeks dropped to a very low level and remained consistent at the low level indicating no delamination. Visual inspection did not reveal any particles in the syringe solution.

FIG. 7 demonstrates the syringe forces for DI water filled syringes that have been treated with a silane coupling agent (0.5% solution of methacryloxypropyl trimethoxy silane in isopropanol) and ethylene plasma pretreated then stored for an extended period (Example 4).

Results:
1. Break-free force—The break-free force of the syringes stored for 6 weeks was approximately half that of the syringes from Example 3.
2. Dynamic force—After reaching the break-free force, the dynamic force of the syringes stored for 6 weeks dropped to a very low level and remained consistent at the low level indicating no delamination. Visual inspection did not reveal any particles in the syringe solution.

CONCLUSIONS

Ethylene plasma pretreatment results in a 60 percent drop in break-free force over untreated syringes when tested empty as well as DI water filled syringes. This indicates that the squeezing action resulting from the compressive forces exerted by the parked stopper do not completely displace the lubricant in the case of the ethylene plasma pretreated syringe barrel indicating better bonding between the lubricant and the pretreated surface.

For DI water filled syringes, the dynamic forces in the case of syringes without ethylene plasma pretreatment rise rapidly to unacceptably high levels, greater than the initial break-free forces. This indicates that the water has displaced the lubricant and the forces increase as the stopper travels down the syringe barrel. In the case of the ethylene plasma pretreated syringes, the dynamic forces are consistently low indicating no displacement of the lubricant induced by the fluid medium. However, after extended storage conditions of up to 6 weeks, which would be common for a prefilled syringe, the ethylene plasma pretreatment fails and is delaminated from the glass surface. This results again in increase in the dynamic syringe forces indicating syringe failure (FIG. 5). This indicates that the ethylene plasma pretreatment only results in a short-term protection but eventually fails when exposed to aqueous based fluids for extended periods.

FIG. 6 demonstrates the use of silane coupling agent treatments and their effectiveness in providing long-term stability to the perfluoropolyether lubricated syringe. Even after storage of 6 weeks at elevated temperatures the syringe performs as desired with consistent dynamic syringe forces without causing any delamination.

Finally, FIG. 7 combines the silane coupling agent treatment and the ethylene plasma pretreatment demonstrating superior bonding of the ethylene plasma pretreatment layer onto the silane coupling agent. The silane coupling agent is used as a tie layer to increase compatibility between the inorganic glass surface and the organic ethylene plasma polymer.

These results clearly show an unexpected but extremely important performance enhancement, particularly for glass syringes that are prefilled with the medicant (fluid) and are stored for an extended period of time before use.

We claim:

1. A method for lubricating a surface, comprising applying a coupling agent to the surface; exposing the applied coupling agent to a first ionizing gas plasma at about atmospheric pressure thereby applying a polymer to the coupling agent; applying a lubricant to the polymer; and exposing the lubricant to a second ionizing gas plasma.

2. The method of claim 1 wherein the surface is a glass surface.

3. The method of claim 1, wherein the first ionizing gas plasmas is comprised of a mixture of a carrier gas and a reactive gas.

4. The method of claim 3 wherein the concentration of the reactive gas in the gas mixture ranges from about 0.001 percent to about 10 percent.

5. The method of claim 3 wherein the carrier gas is selected from one or more groups comprising helium, neon, argon, krypton, xenon, air, oxygen, carbon dioxide, carbon monoxide, water vapor, nitrogen, hydrogen, and mixtures thereof.

6. The method of claim 3 wherein the reactive gas is a hydrocarbon compound.

7. The method of claim 6 wherein the reactive gas is selected from one or more groups comprising an alkane, an alkene, an alkyne, and mixtures thereof.

8. The method of claim 7 wherein the reactive alkane gas is selected from one or more groups comprising methane, ethane, propane, butane, and mixtures thereof.

9. The method of claim 7 wherein the reactive alkene gas is selected from one or more groups comprising ethylene, propylene, isobutylene, and mixtures thereof.

10. The method of claim 7 wherein the reactive alkyne gas is selected from one or more groups comprising ethyne, propyne, 1-butyne, and mixtures thereof.

11. The method of claim 3 wherein the reactive gas is a fluorocarbon compound.

12. The method of claim 11 wherein the fluorocarbon reactive gas is selected from one or more groups comprising tetrafluoromethane, tetrafluoroethylene, hexafluoropropylene, and mixtures thereof.

13. The method of claim 3 wherein the reactive gas is an organometallic compound.

14. The method of claim 13 wherein the organometallic reactive gas is selected from one or more groups comprising tetramethylsilane, hexamethyldisiloxane, and mixtures thereof.

15. The method of claim 1 wherein an amount of time the surface is exposed to the first ionizing gas plasma ranges from about 0.1 second to about 5 minutes.

16. The method of claim 1 wherein an amount of time the surface is exposed to the second ionizing gas plasma ranges from about 0.1 second to about 5 minutes.

17. The method of claim 1, wherein the coupling agent is a silane coupling agent having the general formula R—$(CH_2)_n$—Si—$X_3$, wherein
R is an organofunctional group linked to a silicon atom via a silicon-carbon bond; and
X is a hydrolyzable group capable of forming silanol groups.

18. A method for lubricating a glass surface, comprising applying a silane coupling agent to the glass surface, the silane coupling agent having the general formula R—$(CH_2)_n$—Si—$X_3$, wherein R is an organofunctional group linked to a silicon atom via a silicon-carbon bond and X is a hydrolyzable group capable of forming silanol groups; exposing the silane coupling agent to a first ionizing gas plasma at about atmospheric pressure thereby applying a polymer to the silane coupling agent;

applying a perfluoropolyether lubricant to the polymer surface; and exposing the perfluoropolyether lubricant to a second ionizing gas plasma.

19. A method for lubricating a surface, comprising:
(a) providing the surface;
(b) applying a coupling agent to the surface;
(c) subsequent to applying the coupling agent, applying a lubricant to form a coated surface; and
(d) exposing the coated surface to an ionizing gas plasma at about atmospheric pressure for a predetermined period of time.

20. The method of claim 19, wherein the surface is a glass surface.

* * * * *